United States Patent
Fujimoto (10) Patent No.: US 8,003,049 B2
(45) Date of Patent: Aug. 23, 2011

(54) ANALYZER

(75) Inventor: Koji Fujimoto, Kyoto (JP)

(73) Assignee: Arkray, Inc., Kyoto (JP)

( * ) Notice: Subject to any disclaimer, the term of this patent is extended or adjusted under 35 U.S.C. 154(b) by 524 days.

(21) Appl. No.: 11/664,196

(22) PCT Filed: Sep. 28, 2005

(86) PCT No.: PCT/JP2005/017876
§ 371 (c)(1),
(2), (4) Date: Mar. 29, 2007

(87) PCT Pub. No.: WO2006/035830
PCT Pub. Date: Apr. 6, 2006

(65) Prior Publication Data
US 2008/0019881 A1     Jan. 24, 2008

(30) Foreign Application Priority Data
Sep. 30, 2004   (JP) .................................. 2004-287307

(51) Int. Cl.
*G01N 21/00*    (2006.01)
(52) U.S. Cl. ................ 422/64; 422/63; 422/67; 422/72; 422/50; 436/45; 219/411; 165/263
(58) Field of Classification Search .................... 422/64, 422/63, 67, 72; 219/411; 165/263
See application file for complete search history.

(56) References Cited

U.S. PATENT DOCUMENTS

| | | | |
|---|---|---|---|
| 4,980,538 A * | 12/1990 | Calzi et al. | 219/411 |
| 6,319,469 B1 * | 11/2001 | Mian et al. | 422/64 |
| 6,335,478 B1 * | 1/2002 | Chou et al. | 136/201 |
| 6,633,785 B1 | 10/2003 | Kasahara et al. | |
| 6,880,968 B1 | 4/2005 | Haar | |
| 2003/0082079 A1 | 5/2003 | Sawano | |
| 2004/0012676 A1 | 1/2004 | Weiner et al. | |
| 2005/0282290 A1 | 12/2005 | Fujimoto et al. | |

FOREIGN PATENT DOCUMENTS

| | | |
|---|---|---|
| CN | 2204419 | 8/1995 |
| JP | 2-39212 | 2/1990 |
| JP | 2001-136954 | 2/1990 |
| JP | 9-189703 | 7/1997 |
| JP | 2002-203331 | 1/2002 |
| JP | 2002-90357 | 3/2002 |
| JP | 2002-131201 | 5/2002 |
| JP | 2003-107094 | 4/2003 |
| JP | 2003-513277 | 4/2003 |

(Continued)

*Primary Examiner* — Sally A Sakelaris
(74) *Attorney, Agent, or Firm* — Morgan, Lewis & Bockius LLP (57) ABSTRACT

In an analyzer for analyzing a sample that reacts with a reagent 25, an analyzing tool 10, an infrared sensor 1 and a temperature controlling part 5 are provided. Inside the analyzing tool 10, a reaction cell 24 in which the sample and the reagent 25 react with each other and a heating element 33 that is heated by electrification are provided. The infrared sensor 1 is disposed outside the analyzing tool 10 so as to photoreceive an infrared ray 9 that is emitted from the reaction cell 24, and outputs a signal that is in accordance with an amount of the photoreceived infrared ray 9 to the temperature controlling part 5. The temperature controlling part 5 adjusts a heat value of the heating element 33 based on the signal from the infrared sensor 1.

9 Claims, 7 Drawing Sheets

FOREIGN PATENT DOCUMENTS

| | | |
|---|---|---|
| JP | 2003-126686 | 5/2003 |
| JP | 2004-3989 | 1/2004 |
| JP | 2004-61262 | 2/2004 |
| WO | 97/21090 | 6/1997 |
| WO | 03/093836 | 11/2003 |
| WO | 2004/016948 | 2/2004 |

* cited by examiner

ANALYZER

TECHNICAL FIELD

The present invention relates to an analyzer for analyzing a sample that reacts with a reagent, and particularly relates to an analyzer utilizing an analyzing tool such as a microdevice.

BACKGROUND ART

Recently, in order to enable an analysis by using a small amount of a sample, an analyzing tool called a microdevice has been developed keenly. The microdevice is manufactured by, for example, forming a fine channel (a width thereof ranges from several μm to several hundreds μm) and a concave part on one surface of a glass substrate or a resin substrate by utilizing a micromachining technique applied to an integrated circuit (for example, see Patent Document 1).

Figure 7:
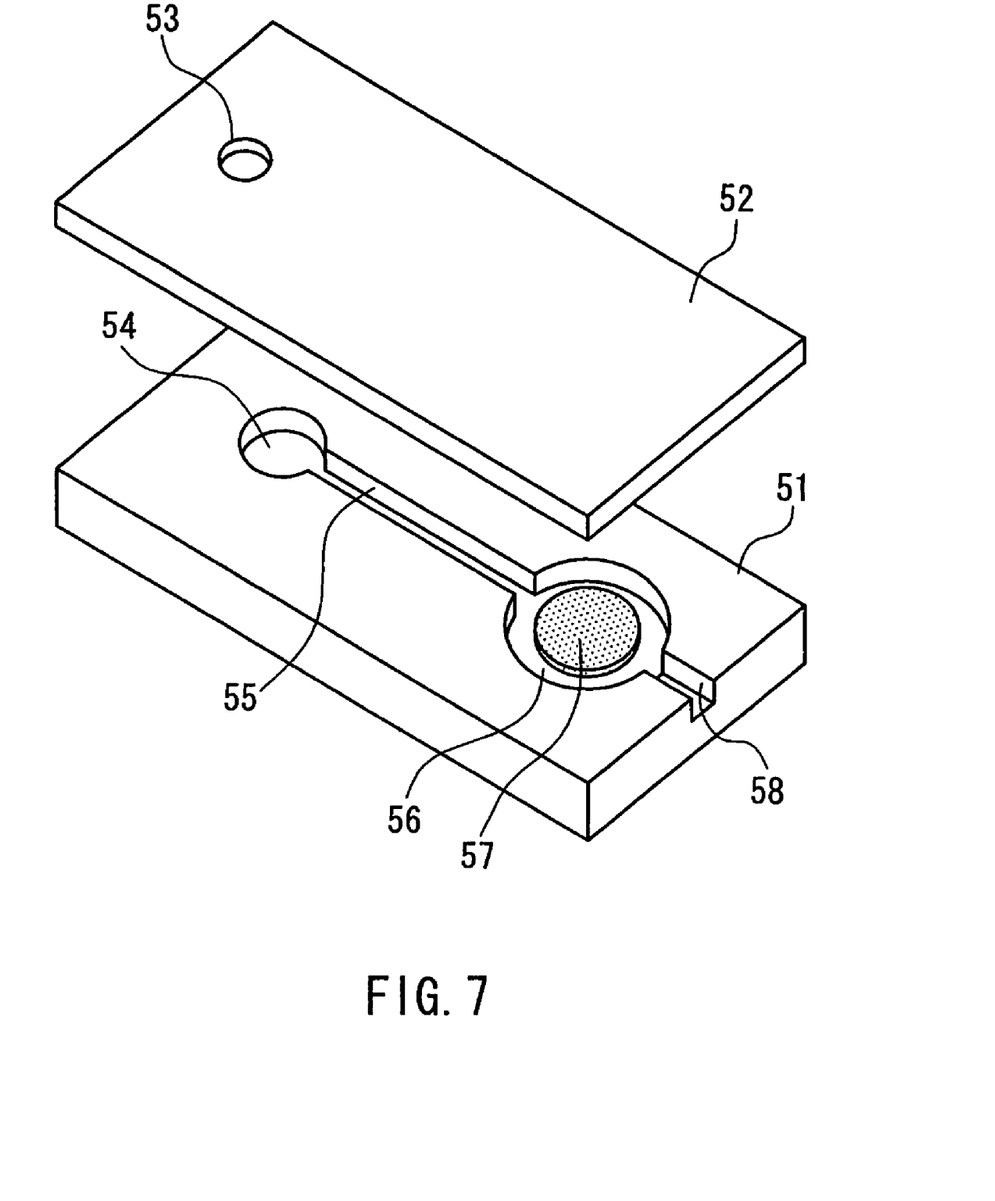
FIG. 7 is an exploded perspective view showing an example of a conventional microdevice.

FIG. 7 is an exploded perspective view showing an example of a conventional microdevice. As shown in FIG. 7, the microdevice is formed by connecting a substrate 51 and a cover 52. The substrate 51 and the cover 52 are formed of an optically transparent material such as a transparent resin and a glass.

Moreover, as shown in FIG. 7, in the cover 52, an inlet 53 that pierces the cover 52 in its thickness direction is formed. The inlet 53 is used for introducing a sample such as blood into an inside of the microdevice. On one surface of the substrate 51, a concave part 54 that has a circular-shaped cross section, a concave part 56 that has a larger cross section than that of the concave part 54, and a channel 55 that connects the concave part 54 and the concave part 56 are provided.

The concave part 54 is formed so as to conform to the inlet 53 of the substrate 51. The concave part 54 functions as a storage part for storing the introduced sample temporarily. In the concave part 56, a solid reagent 57 is disposed. The concave part 56 functions as a reaction cell. The channel 55 functions as a flow path for transferring the sample that is stored in the concave part 54 to the concave part 56.

Moreover, in order to secure ventilation between the concave part 56 and an outside when connecting the substrate 51 and the cover 52, a channel 58 serving as a vent path also is formed on the substrate 51. According to such a structure, in the microdevice shown in FIG. 7, the sample transfers from the concave part 54 to the concave part 56 by utilizing capillary action. Further, the reagent 57 is colored by reacting with a certain component in the sample. Accordingly, if measuring absorbance by irradiating the concave part 56 that serves as the reaction cell with light from the cover 52 side and photo-receiving transmitted light, the density of the certain component in the sample can be determined.

Moreover, in the chemical analysis using the microdevice, which is represented by the example of FIG. 7, temperature control of the reaction cell of the microdevice is important for maintaining a condition of the reaction to be constant. As one method for controlling the temperature of the reaction cell of the microdevice, a method using a heater block is known. According to this method, a whole of the microdevice can be heated uniformly.

However, in the case of using the heater block, the heater block is required to have a sufficiently large heat capacity with respect to a heat capacity of the microdevice. Further, the size of the heater block is in proportion to the heat capacity thereof. Thus, the temperature control using the heater block has problems in that an increase of a size of a measurement apparatus cannot be avoided, and the consumption of an electric power cannot be reduced. Moreover, because of heating from an outside of the microdevice, a temperature of the reaction cell inside the microdevice is expected only from a time of increasing a temperature and a temperature controlling precision of the heater block, and thus it is difficult to control the temperature of the reaction cell strictly.

Whereas, a method in which a metal thin film serving as a heating element and a temperature sensor (a temperature measurement device) such as a thermocouple and a thermistor element are provided inside the microdevice, which are used for heating and measuring the temperature inside the microdevice so as to achieve the temperature control also is known (for example, see Patent Document 2). According to this temperature controlling method, the size of the measurement apparatus can be decreased, and the consumption of electric power can be reduced. Further, since the microdevice can be heated from its inside, and the temperature thereof can be measured inside the microdevice, the temperature control of the reaction cell can be achieved more strictly, compared with the case of using the heater block.

Patent Document 1: WO 03/093836 brochure (FIGS. 1 to 40 and 45 to 48)

Patent Document 2: JP 2002-90357 A (FIG. 1)

DISCLOSURE OF INVENTION

Problem to be Solved by the Invention

However, in the case of providing the temperature sensor inside the microdevice, since an electric wire from the temperature sensor is extended from the inside of the microdevice toward the outside thereof, the heat inside the microdevice is transmitted via the electric wire and is discharged toward the outside. Accordingly, the temperature of the reaction cell that is measured by using the temperature sensor is lower than an actual temperature of the reaction cell. Thus, also in the temperature controlling method using the above-described heating element and the temperature sensor, it is difficult to measure the temperature inside the reaction cell precisely, and thus the temperature control is not sufficient.

Moreover, in some cases, a plurality of the reaction cells are provided in order to perform a plurality of kinds of tests with respect to one sample, and in such cases, it is necessary to provide the temperature sensor in each of the reaction cells. However, since the temperature sensors generally have variations, in the case of using the temperature sensors, it is required to precisely correct the temperatures that are measured by the respective temperature sensors, in order to measure the temperatures inside the respective reaction cells precisely.

Moreover, although a volume of the reaction cell is required to be decreased, a decrease in size of the temperature sensor is limited. Thus, the volume of the temperature sensor may be equivalent to or larger than the volume of the reaction cell. In this case, the temperature sensor absorbs the heat, and may cause a problem of affecting the temperature to be measured.

Moreover, the microdevice is required to be disposable in the light of the ease of handling. However, in the case of providing the temperature sensor inside the microdevice, since the cost of the microdevice is increased, it is difficult to make the microdevice to be disposable.

It is an object of the present invention is to solve the above-described problems, and to provide the analyzer that can measure the temperature of the reaction cell provided inside the analyzing tool precisely, and can achieve the temperature control more strictly, compared with a conventional one.

Means for Solving Problem

In order to attain the objects described above, the analyzer of the present invention is an analyzer for analyzing a sample that reacts with a reagent, the analyzer including: an analyzing tool; an infrared sensor; and a temperature controlling part, wherein the analyzing tool includes: a reaction cell in which the sample and the reagent react with each other; and a heating element that is heated by electrification, inside the analyzing tool, the infrared sensor is disposed outside the analyzing tool so as to photoreceive an infrared ray that is emitted from the reaction cell, and outputs a signal that is in accordance with an amount of the photoreceived infrared ray to the temperature controlling part, and the temperature controlling part adjusts a heat value of the heating element based on the signal from the infrared sensor.

Effects of the Invention

As described above, the analyzer of the present invention measures the temperature of the reaction cell by photoreceiving the infrared ray that is emitted from the reaction cell by using the infrared sensor. Thus, compared with a conventional analyzer, the temperature inside the reaction cell can be measured more precisely. As a result, by using the analyzer of the present invention, more strict temperature control can be achieved, compared with the conventional one. Moreover, since the temperature sensor is not required to be provided in the analyzing tool, it also is easy to make the analyzing tool disposable.

DESCRIPTION OF THE INVENTION

The analyzer of the present invention is an analyzer for analyzing a sample that reacts with a reagent, the analyzer including: an analyzing tool; an infrared sensor; and a temperature controlling part, wherein the analyzing tool includes: a reaction cell in which the sample and the reagent react with each other; and a heating element that is heated by electrification, inside the analyzing tool, the infrared sensor is disposed outside the analyzing tool so as to photoreceive an infrared ray that is emitted from the reaction cell, and outputs a signal that is in accordance with an amount of the photoreceived infrared ray to the temperature controlling part, and the temperature controlling part adjusts a heat value of the heating element based on the signal from the infrared sensor.

In the analyzer of the present invention, it is preferable that the analyzing tool is formed of an optically transparent material, and further includes: an inlet for introducing the sample into an inside of the analyzing tool; a storage part for storing the introduced sample temporarily; and a flow path for transferring the stored sample into the reaction cell. Moreover, in this case, it is preferable that the analyzing tool is formed to have a disk shape, the inlet and the storage part are disposed so as to be positioned at a center of the disk, a plurality of the reaction cells are provided, each of the reaction cells is disposed on a periphery of the storage part along a circumferential direction of the disk, and a plurality of the flow paths are provided in a radial manner. In this case, a plurality of analyses can be performed with respect to one sample at one time.

Moreover, in the analyzer of the present invention, it is preferable that the infrared sensor is disposed at a position that faces the reaction cell in a thickness direction of the analyzing tool in a state where a photoreceptive surface of the infrared sensor faces the reaction cell, and a thickness of the analyzing tool in a part where the reaction cell is provided on the infrared sensor side is set within a range from 0.01 mm to 5 mm. Further, in this case, it is preferable that a distance between the photoreceptive surface of the infrared sensor and the analyzing tool is set within a range from 0.1 mm to 30 mm. According to these cases, precision for measuring the temperature can be enhanced. Moreover, as the infrared sensor, a thermopile-type infrared sensor can be used.

Moreover, it is preferable that the analyzer of the present invention includes a measurement apparatus for measuring the reactivity of the sample that reacts with the reagent in the reaction cell, wherein the temperature controlling part specifies a temperature of the reaction cell based on the signal that is output from the infrared sensor to the temperature controlling part, and notifies the specified temperature to the measurement apparatus, and the measurement apparatus corrects the measured reactivity based on the temperature that is notified by the temperature controlling part.

According to the above-described case, more precise measurement results can be obtained. Moreover, in the above-described case, it is possible that the measurement apparatus includes a memory part for storing a correction factor group that is set for each temperature, specifies a corresponding correction factor among the stored correction factor group based on the temperature that is notified by the temperature controlling part, and multiplies the specified correction factor by the measured reactivity so as to correct the measured reactivity.

Moreover, it is preferable that the analyzer of the present invention includes a measurement apparatus for measuring the reactivity of the sample that reacts with the reagent in the reaction cell, wherein the analyzing tool includes a blocking part for blocking an inflow of the sample into the reaction cell, the temperature controlling part specifies a temperature of the reaction cell based on a signal that is output from the infrared sensor to the temperature controlling part, and notifies the specified temperature to the measurement apparatus, and the measurement apparatus cancels the blocking by the blocking part when the temperature that is notified by the temperature controlling part reaches a reference temperature.

In the above-described case, the sample is introduced into the reaction cell after a temperature of the reaction cell reaches the reference temperature. Thus, in particular, in the case where the reagent is disposed in the reaction cell in a state of being solidified, since a speed of dissolving or dispersing the reagent into the sample can be maintained to be constant, the reaction with excellent reproducibility can be realized. Further, in the case of specifying a density of an object material by measuring a reaction speed, like the measurement of some enzyme activities, if the temperature of the reaction cell has a deviation between a time when starting the measurement and a time when terminating the measurement, it is difficult to measure a reaction speed precisely. Whereas, according to the above-described case, the temperature of the reaction cell easily can be maintained to be constant from the time when starting the measurement to the time when terminating the measurement. The above-described case also is applied effectively to such measurement of the reaction speed.

Also, it also is preferable that the analyzer of the present invention further includes: a case for storing the infrared sensor; a heater for heating the case; and a temperature sensor for outputting a case temperature notifying signal that depends on a temperature of the case to the temperature controlling part, and the temperature controlling part drives the heater based on the signal from the temperature sensor, and adjusts a temperature of the infrared sensor. According to this case, since the temperature of the infrared sensor can be maintained to be constant, the temperature of the reaction cell can be specified more precisely.

Embodiment 1

Figure 1:
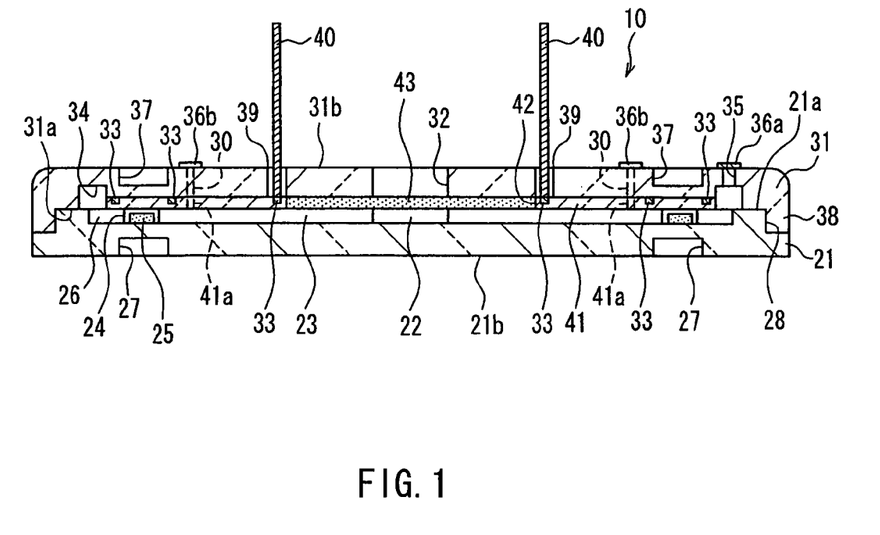
FIG. 1 is a cross-sectional view showing an example of an analyzing tool that is used in an analyzer of Embodiment 1 of the present invention.
Figure 2:
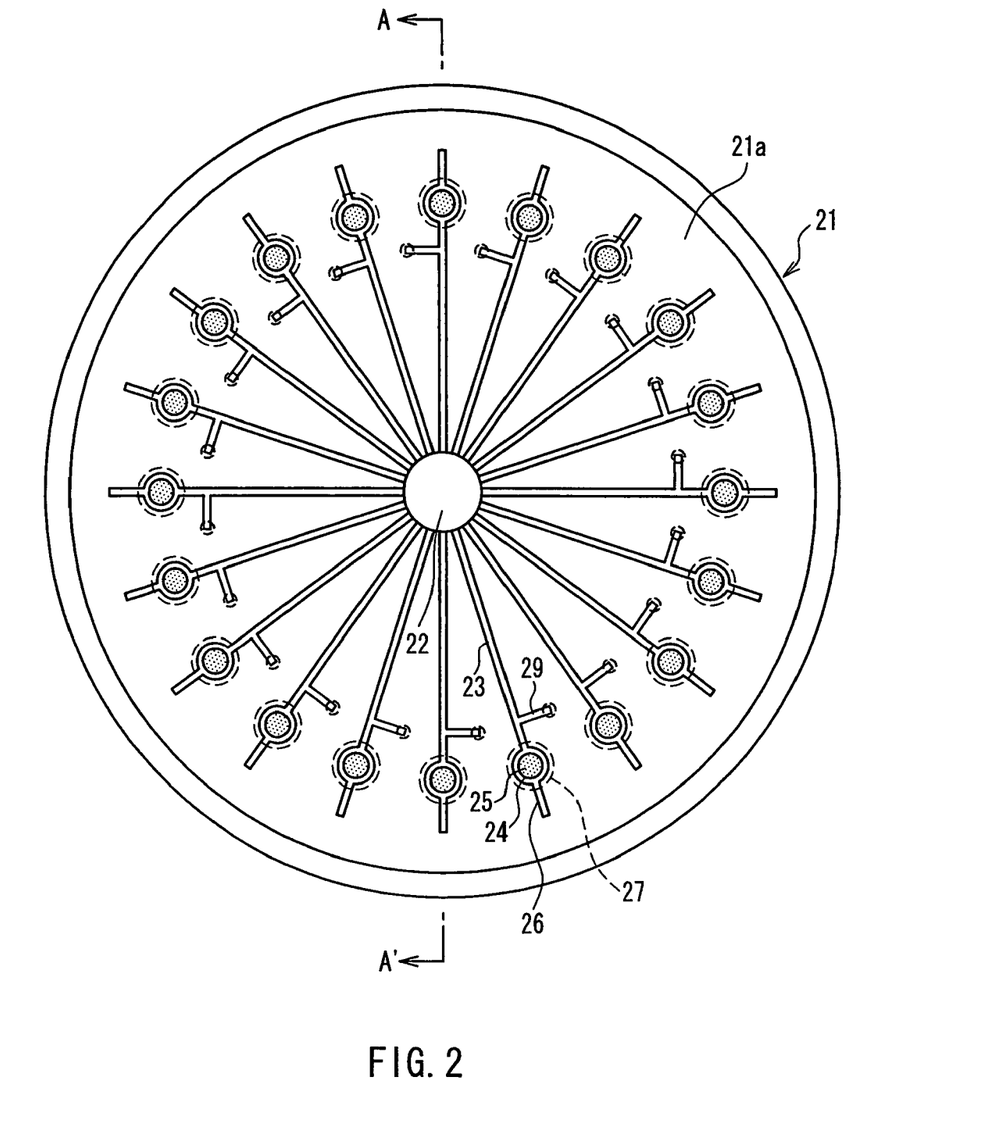
FIG. 2 is a top view showing a substrate that composes the analyzing tool shown in FIG. 1.
Figure 3:
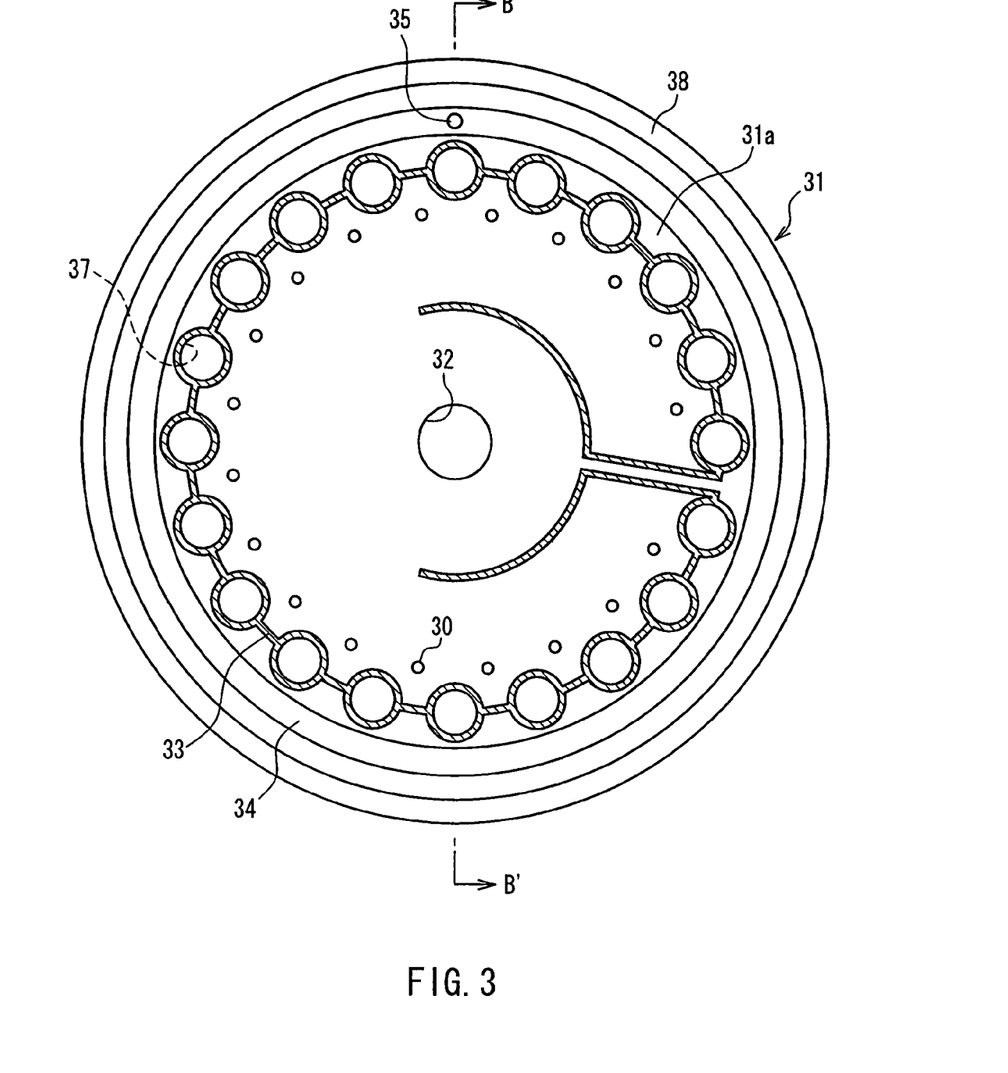
FIG. 3 is a bottom view showing a cover that composes the analyzing tool shown in FIG. 1.
Figure 4:
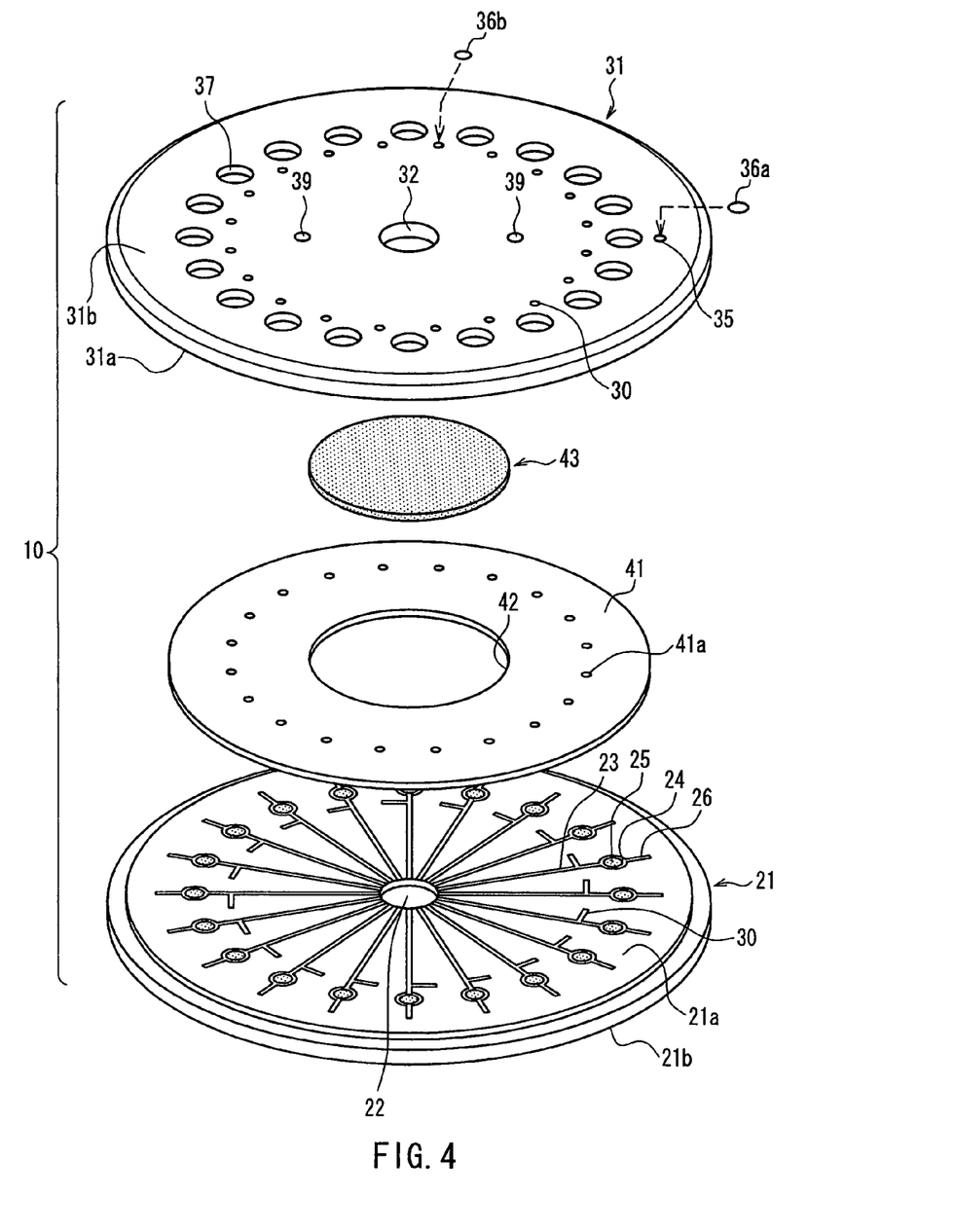
FIG. 4 is an exploded perspective view of the analyzing tool shown in FIG. 1.

An analyzer of Embodiment 1 of the present invention will be described below with reference to drawings. Firstly, an example of an analyzing tool used in the analyzer of Embodiment 1 will be described with reference to FIGS. 1 to 4. FIG. 1 is a cross-sectional view showing an example of the analyzing tool that is used in the analyzer of Embodiment 1 of the present invention. FIG. 2 is a top view showing a substrate that composes the analyzing tool shown in FIG. 1. FIG. 3 is a bottom view showing a cover that composes the analyzing tool shown in FIG. 1. FIG. 4 is an exploded perspective view of the analyzing tool shown in FIG. 1.

It should be noted that the cross section shown in FIG. 1 is taken along a line A-A' shown in FIG. 2 and a line B-B' shown in FIG. 3. Moreover, FIG. 2 shows a connection surface (a surface on a cover side) 21a of a substrate 21, and FIG. 3 shows a connection surface (a surface on the substrate side) 31a of the cover 31.

As shown in FIGS. 1 to 4, in Embodiment 1, an analyzing tool 10 is called a microdevice, which is manufactured by utilizing a micromachining technique applied to a semiconductor integrated circuit. As shown in FIGS. 1 and 4, the analyzing tool 10 has the substrate 21 and the cover 31. The substrate 21 and the cover 31 are formed of an optically transparent material. In the present example, the substrate 21 and the cover 31 are formed to have disk shapes (see FIGS. 2 to 4).

As shown in FIGS. 1, 2 and 4, on the connection surface 21a of the substrate 21, a storage part 22, a flow path 23, a reaction cell 24 and a vent path 26 are formed. Moreover, on the connection surface 21a, a self-adherent elastomer sheet 41 is attached. Further, in the present example, since blood that is collected from a patient is used as a sample, a separation film 43 (see FIGS. 1 and 4) for separating a blood cell component in the blood is fit in a hole 42 that is formed at a center of the elastomer sheet 41. Thus, upper sides of the storage part 22, the flow path 23, the reaction cell 24 and the vent path 26 are enclosed by the elastomer sheet 41 and the separation film 43. Incidentally, the elastomer sheet 41 also is formed of an optically transparent material.

The storage part 22 is used for temporarily storing blood that is introduced into an inside of the analyzing tool 10. In the present example, the storage part 22 is disposed at a center of the substrate 21. Moreover, the storage part 22, the separation film 43 and an inlet 32 described below conform to each other at a center of the analyzing tool 10.

The reaction cell 24 is used for a reaction between the sample and a reagent 25. In the present example, a plurality of the reaction cells 24 are provided, and are arranged on a periphery of the storage part 22 at a constant interval along a circumferential direction of the substrate 21. Inside the reaction cell 24, the solid reagent 25 is disposed.

As shown in FIG. 2, in Embodiment 1, the reagent 25 is disposed in all of the reaction cells 24, but it also is possible that the reagent 25 is not disposed in some of the reaction cells 24. In this case, the reaction cells 24 in which the reagent 25 is not disposed can be used for, for example, measurement of a blank value that is necessary for calculating absorbance. Moreover, the reagent 25 that is disposed in the respective reaction cells 24 may be of different kinds.

The flow path 23 is used for transferring the sample that is stored in the storage part 22 into the reaction cells 24. In Embodiment 1, the flow path 23 is a channel to communicate the storage part 22 with each of the reaction cells 24, and is formed in a radial manner on the connection surface 21a of the substrate 21. Moreover, the vent path 26 also is a channel that is formed on the connection surface 21a similarly to the flow path 23. The vent path 26 is communicated with a channel 34 (see FIGS. 1 and 3) that is formed on the cover 31 when connecting the substrate 21 and the cover 31, and is used for securing ventilation between the reaction cell 24 and the outside. This point will be described below. In Embodiment 1, the vent path 26 is provided on an extension of the flow path 23.

Moreover, in Embodiment 1, on the connection surface 21a of the substrate 21, a branch path 29 also is formed for each of the flow paths 23. Each of the branch paths 29 is branched from a part of the corresponding flow path 23 on the reaction cell 24 side. The branch path 29 also is a channel that is formed on the connection surface 21a similarly to the flow path 23. Moreover, the branch path 29 is communicated with a through hole 30 (see FIGS. 1 and 3) that is formed on the cover 31 when connecting the substrate 21 and the cover 31. The branch path 29 is used for securing ventilation between the flow path 23 and the outside. This point will be described below.

Incidentally, as described above, the formation of the storage part 22, the flow path 23, the reaction cell 24, the vent path 26 and the branch path 29 on the substrate 21 are achieved by utilizing the micromachining technique applied to a semiconductor integrated circuit. Specifically, the formation of the storage part 22, the flow path 23, the reaction cell 24, the vent path 26 and the branch path 29 are achieved by forming resist patterns that correspond to shapes of them on the connection surface 21a of the substrate 21 by photolithography, and subsequently performing dry etching or wet etching.

As shown in FIGS. 1 and 3, in Embodiment 1, the cover 31 is provided with the inlet 32 for introducing the sample into the inside of the analyzing tool 10. As described above, the inlet 32 is provided at a center of the cover 21 so as to conform to the separation film 42 and the storage part 22. Moreover, on the connection surface 31a of the cover 31, a heating element 33 that is heated by electrification is provided. In FIG. 3, the heating element 33 is hatched.

Moreover, in Embodiment 1, the heating element 33 is a conductive thin film that is formed of a metal material such as silver, aluminum and copper, a carbon or the like, and constitutes one wiring. The formation of the heating element 33 can be achieved by, for example, vapor deposition or printing. Incidentally, in the example of FIG. 3, the heating element 33 is formed on the connection surface 31a of the cover 31, but also can be formed on, for example, a surface of the elastomer sheet 41 on the cover 31 side.

Moreover, the heating element 33 also can be formed by utilizing the micromachining technique applied to a semiconductor integrated circuit. In this case, a thin film firstly is formed on the connection surface 31a of the cover 31 by spattering. Next, a resist pattern that conforms to the heating element 33 to be formed is formed thereon by photolithography. Thereafter, a redundant thin film that is not covered with the resist pattern is removed by etching, thereby obtaining the heating element 33.

Moreover, in Embodiment 1, as shown in FIG. 3, the heating element 33 is formed such that each of the reaction cells 24 appears to be surrounded by the heating element 33 when viewing the analyzing tool 10 from an upper side or a lower side thereof, in order to uniformalize temperatures of the respective reaction cells 24. Incidentally, in the present invention, a pattern to form the heating element 33 is not limited particularly. The heating element 33 may be formed such that the sample can be heated also in the flow path 23, for example.

Moreover, as shown in FIG. 1, an electric power is supplied to the heating element 33 by two electrode pins 40. The electrode pins 40 are connected with the heating element 33 via insertion holes 39 that are formed in the cover 31, respectively. Further, one of the insertion holes 39 is formed so as to conform to one end of the heating element 33, and the other one of the insertion holes 39 is formed so as to conform to the other end of the heating element 33.

Moreover, in Embodiment 1, as shown in FIGS. 1 and 3, a ring-shaped channel 34 is formed on the connection surface 31a of the cover 31. The channel 34 is communicated with the vent path 26 that is provided on the substrate 21 when connecting the substrate 21 and the cover 31. Further, a through hole 35 that pierces the cover 31 in its thickness direction, and is communicated with the channel 34 also is formed in the cover 31. Thus, through the vent path 26, the channel 34 and the through hole 35, ventilation between each of the reaction cells 24 and the outside is secured.

Further, in Embodiment 1, as shown in FIGS. 1, 3 and 4, a plurality of through holes 30 that pierce the cover 31 in its thickness direction are formed along the circumferential direction in the cover 31. Moreover, each of the plurality of the through holes 30 is communicated with any of the branch paths 29 that are provided on the substrate 21. Further, also in the elastomer sheet 41, a plurality of through holes 41a (see FIGS. 1 and 4) are formed so as to be communicated with the respective through holes 30. Thus, through the branch paths 29, the through holes 30 and the through holes 41a, ventilation between each of the flow paths 23 and the outside is secured.

It should be noted that, as shown in FIGS. 1 and 4, openings of the through holes 35 on the outside are enclosed by seals 36a in a state where the sample is not introduced. Similarly, openings of the through holes 30 on the outside also are enclosed by seals 36b. Thus, even when introducing a predetermined amount of the sample from the inlet 32, the sample is just stored in the storage part 22, and an inflow of the sample into the flow path 23 and the reaction cell 24 is blocked.

Moreover, in a state of where the storage part 22 stores the sample, when breaking or releasing the seals 36b for enclosing the openings of the through holes 30, the sample flows into the flow path 23 by capillary action, and reaches a connection part between the flow path 23 and the branch path 29. Subsequently, when breaking or releasing the seals 36a for enclosing the openings of the through holes 35, the sample flows into the reaction cell 24 by capillary action, and reacts with the reagent 25.

As described above, in Embodiment 1, the branch paths 29, the through holes 30, the through holes 41a and the seals 36b function as a first blocking part for blocking the inflow of the sample into the flow paths 23. Moreover, the vents 26, the channel 34, the through holes 35 and the seals 36a function as a second blocking part for blocking the inflow of the sample into the reaction cells 24. Moreover, the blocking by the first blocking part can be cancelled by the breaking or the releasing of the seal 36b, and the blocking by the second blocking part can be cancelled by the breaking or the releasing of the seal 36a.

In Embodiment 1, the seals 36a and 36b are not limited particularly, as long as they can enclose the openings of the through holes 30 or the through holes 35 reliably, and can be broken or released easily. In Embodiment 1, the seals 36a and 36b are formed of a metal foil such as an aluminum foil or a resin film such that they can be broken easily by irradiation of a laser beam or puncturing by a needle. Moreover, in Embodiment 1, the seals 36a and 36b are attached on the cover 31 by adhesion of an adhesive or fusion.

Moreover, in Embodiment 1, as shown in FIGS. 1 and 3, a plurality of concave parts 37 are formed on a surface (an external surface) 31b of the cover 31 on the opposite side of the connection surface 31a, at positions conforming to the respective reaction cells 24. A bottom surface of the concave part 37 serves as an incident surface when below-described light for analysis is incident into the analyzing tool 10. Similarly, as shown in FIGS. 1 and 2, a plurality of concave parts 27 are formed also on a surface (an external surface) 21b of the substrate 21 on the opposite side of the connection surface 21a, at positions conforming to the respective reaction cells 24. A bottom surface of the concave part 27 serves as an exit surface for transmitted light that transmits through the reaction cell 25.

It should be noted that, in Embodiment 1, a whole of the analyzing tool 10 is formed of an optically transparent material, but is not limited to this. Only a part that serves as an incident path of the light into the reaction cell 24, and a part that serves as an exit path of the light from the reaction cell 24 may be formed of the optically transparent material. Specifically, a part from the bottom surface of the concave part 37 to the reaction cell 24, and a part from the reaction cell 24 to the bottom surface of the concave part 27 may be formed of the optically transparent material.

Moreover, as shown in FIGS. 1 to 3, in Embodiment 1, a step 28 is provided in a part on an edge side of the connection surface 21a of the substrate 21. In addition, in a part on an edge side of the connection surface 31a of the cover 31, a ring-shaped convex part 38 is provided so as to be engaged with the step 28. Thus, the substrate 21 and the cover 31 can be positioned easily.

Figure 5:
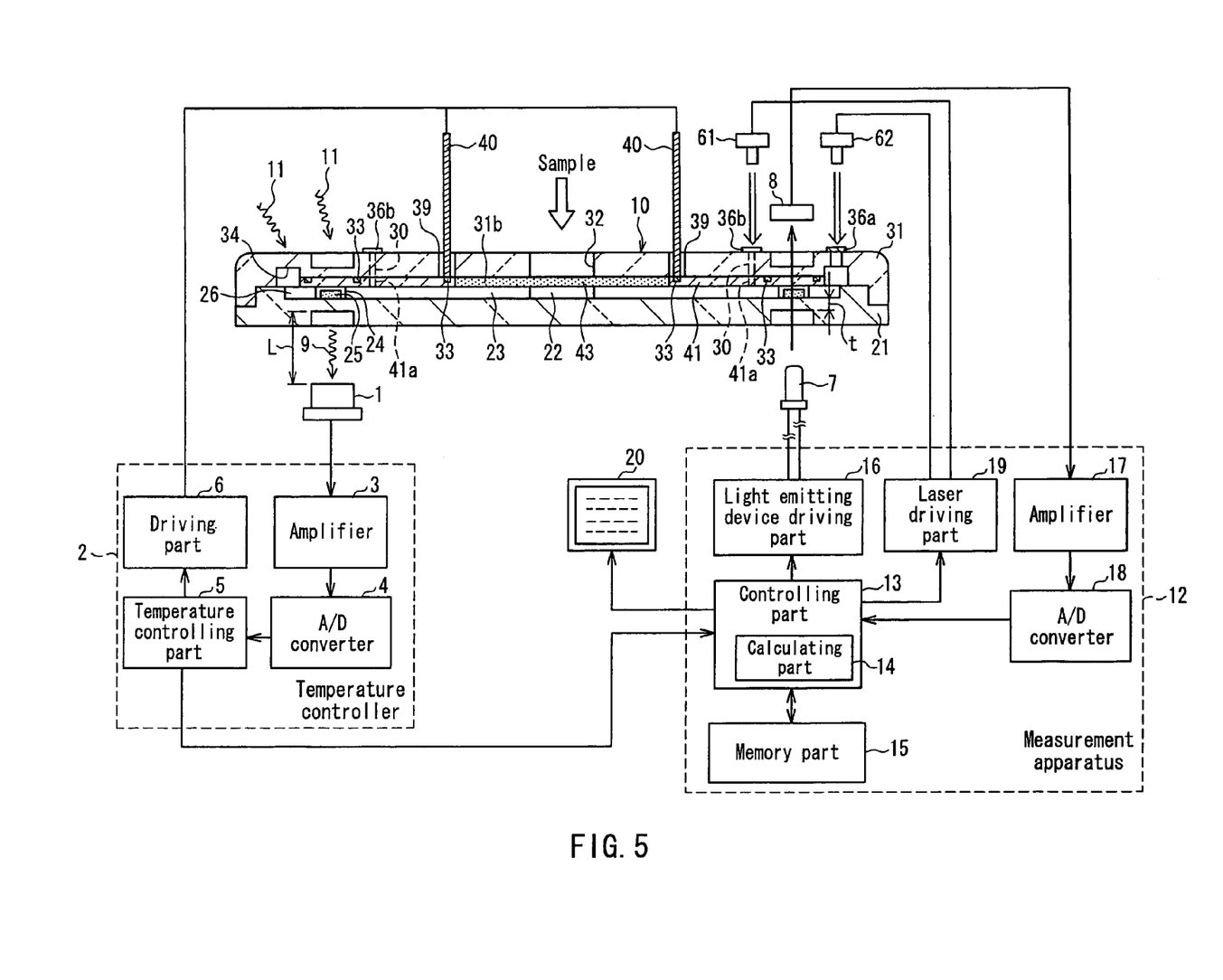
FIG. 5 is a diagram schematically showing a structure of an analyzer of Embodiment 1 of the present invention.

Next, a structure of the analyzer of Embodiment 1 of the present invention and an analysis of the sample using this analyzer will be described with reference to FIG. 5. FIG. 5 is a diagram schematically showing the structure of the analyzer of Embodiment 1 of the present invention.

The analyzer of Embodiment 1 shown in FIG. 5 is an apparatus for measuring reactivity of the sample that reacts with the reagent 25 in each of the reaction cells 24 of the analyzing tool 10 shown in FIGS. 1 to 4, and analyzing a component thereof based on the measured reactivity. In Embodiment 1, the analyzer is provided with a measurement apparatus 12 for measuring absorbance and analyzing a component thereof based on the measured absorbance. Moreover, the analyzer also is provided with a rotation mechanism for rotating the analyzing tool 10 in order to switch the reaction cell 24 whose absorbance is measured, which is not illustrated in FIG. 5.

Moreover, in order to measure precise absorbance, it is important to control the temperatures of the reaction cells 24. Thus, the analyzer shown in FIG. 5 further is provided with an infrared sensor 1 and a temperature controller 2, and controls the temperatures of the reaction cells 24 by using them.

As shown in FIG. 5, the infrared sensor 1 photoreceives an infrared ray 9 that is emitted from the reaction cell 24, and outputs a signal depending on an amount of the photoreceived infrared ray 9 to the temperature controller 2. In Embodiment 1, the infrared sensor 1 is a thermopile-type infrared sensor that is provided with a plurality of thin film thermocouples (not illustrated). The infrared sensor 1 outputs, as a thermal electromotive force of the thermocouple, a temperature change that occurs inside the sensor according to the amount of the photoreceived infrared ray. Also, the infrared sensor 1 is provided with a thermistor (not illustrated) for temperature compensation.

The temperature controller 2 is provided with an amplifier 3, an A/D converter 4, a temperature controlling part 5 and a driving part 6. The amplifier 3 is an amplifying circuit for amplifying the signal from the infrared sensor 1. The amplified signal is input into the A/D converter 4. The A/D converter 4 is an A/D converting circuit for converting the input signal into a digital signal. The digital signal is input into the temperature controlling part 5.

The temperature controlling part 5 detects the temperature of the reaction cell 24 from the input digital signal, and provides an instruction to the driving part 6 based on the detected temperature. The driving part 6 adjusts the amount of an electric power to be supplied to the heating element 33 according to the instruction from the temperature controlling part 5, and adjusts a heat value of the heating element 33. Moreover, the temperature controlling part 5 outputs a signal (a cell temperature notifying signal) for specifying the temperature of the reaction cell 24 to the measurement apparatus 12, in order to notify the temperature of the reaction cell 24 to the measurement apparatus 12. Further, the cell temperature notifying signal is output per each reaction cell, and also includes information for specifying the cell whose temperature is measured.

As described above, in the analyzer of Embodiment 1, the temperature of the reaction cell 24 is measured based on the temperature information from the infrared sensor 1. Thus, unlike the case of measuring the temperature by using the temperature sensor that is described in Background Art, the heat in the reaction cell 24 is not discharged toward the outside via the wirings. Thus, the temperature information that is obtained from the infrared sensor 1 is more precise than the temperature information that is obtained in the case of attaching the temperature sensor in a peripheral region of the reaction cell inside the analyzing tool.

Moreover, in the analyzer of Embodiment 1, since the temperature sensor is not used, an error resulted from the variation of the temperature sensors is not necessary to be corrected. Further, the heat of the object to be measured is not absorbed by the temperature sensor. Moreover, since the cost of the analyzing tool 10 can be saved to be low, the analyzing tool 10 can be disposable. By using the analyzer shown in FIG. 5, the temperature control of the reaction cell 24 can be achieved more strictly, compared with the conventional one.

The measurement apparatus 12 is provided with a light emitting device 7 for irradiating the reaction cell 24 with light, a photoreceptive device 8 for photoreceiving the transmitted light that transmits the reaction cell 24, a controlling part 13 including a calculating part 14, a memory part 15, a light emitting device driving part 16, an amplifier 17 and an A/D converter 18, for measuring the absorbance.

The light emitting device driving part 16 supplies the electric power to the light emitting device 7 according to the instruction from the controlling part 13, and allows the light emitting device 7 to irradiate light. When the light emitting device 7 irradiates the light, the photoreceptive device 8 outputs an analog signal depending on an amount of the photoreceived transmitted light to the amplifier 17. The amplifier 17 amplifies the analog signal, and outputs the amplified analog signal to the A/D converter 18. The A/D converter 18 converts the input signal into a digital signal similarly to the A/D converter 4. The digital signal is input into the controlling part 13.

When the digital signal is input from the A/D converter 18, the calculating part 14 calculates absorbance based on this digital signal. Further, the calculating part 14 calculates the density of a component (or example, an enzyme or the like) to be measured from the calculated absorbance, and allows a display 20 to display the calculated result.

By the way, in the case where a plurality of the reaction cells 24 are provided in the analyzing tool 10 as shown in FIGS. 1 to 4, the temperatures of the respective reaction cells 24 may vary slightly. Moreover, the value of the absorbance may be affected by the temperature of the reaction cell 24. Thus, in Embodiment 1, the calculating part 14 corrects the reactivity of the sample that reacts with the reagent, for example, the absorbance or a density of a component that is calculated from the absorbance, based on the temperature of the reaction cell 24.

Specifically, the calculating part 14 specifies the temperature of the reaction cell whose absorbance is calculated, based on the cell temperature notifying signal that is output from the temperature controller 2. Moreover, when the temperature controlling part 5 outputs the cell temperature notifying signal, the calculating part 14 allows the memory part 15 to store the temperature that is specified by the cell temperature notifying signal and the information for specifying the cell whose temperature is measured. Thus, the calculating part 14 reads out, from the memory part 15, the temperature of the reaction cell whose absorbance is measured, each time when measuring the absorbance.

Moreover, in Embodiment 1, the memory part 15 stores a correction factor group that is set at each temperature. The calculating part 14 reads out a correction factor that corresponds to the temperature of the reaction cell among the correction factor group, and divides the absorbance or the density of the component by the correction factor that is read out, thereby achieving correction.

Table 1 shows an example of the correction factor group that is used in Embodiment 1. The component to be measured in Table 1 is AST (aspartate aminotransferase). Moreover, the correction factor described in Table 1 is a relative density with reference to a density of the component at a reference temperature (37° C.). Thus, in the case of using the correction factor group described in Table 1, the calculating part 14 divides the density of the component obtained by the absorbance by the correction factor.

TABLE 1

| [Measurement item: AST] | |
|---|---|
| temperature [° C.] | correction factor (relative density) |
| 25 | 0.50 |
| 30 | 0.67 |
| 37 | 1.00 |

For example, in the case where the component to be measured is AST, and the temperature of the reaction cell to be measured is 25° C., the calculating part 14 specifies the correction factor as "0.50", and divides the calculated density of the component by "0.50". The calculating part 14 allows the display 20 to display the divided density of the component.

As described above, according to Embodiment 1, the measurement result also can be corrected according to the temperature of the reaction cell 24, and a more precise measurement result can be obtained. It should be noted that, in Embodiment 1, the temperature measurement by using the infrared sensor 1 and the temperature controller 2 is performed before the measurement of the absorbance, but the present invention is not limited to this. In the present invention, the temperature measurement by using the infrared sensor 1 and the temperature controller 2 also may be performed during or after the measurement of the absorbance.

Moreover, as shown in FIG. 5, in Embodiment 1, the measurement apparatus 12 also is provided with a function to cancel the blocking by the first blocking part and the second blocking part of the analyzing tool 10 described above. Specifically, as shown in FIG. 5, the measurement apparatus 12 is provided with lasers 61 and 62 and a laser driving part 19.

The laser 61 is disposed such that the seal 36b is irradiated with its laser beam. The laser 62 is disposed such that the seal 36a is irradiated with its laser beam. The laser driving part 19 supplies electric power to lasers 61 and 62 according to the instruction from the controlling part 13, and allows the lasers 61 and 62 to irradiate with laser beams. Incidentally, in the example of FIG. 5, the two lasers are provided, but the present invention is not limited to this. For example, only one laser movable may be provided.

Thus, the measurement apparatus 12 can measure the reactivity in procedures described below. Firstly, when the sample is stored in the storage part 22, the controlling part 13 allows the laser driving part 19 to drive the laser 61 so as to irradiate the seal 36b with its laser beam. When the seal 36b is broken, the sample flows into a branched part between the flow path 23 and the branch path 29.

Next, the measurement apparatus 12 specifies the temperatures of the respective vacant reaction cells 24 in which the sample is not present, based on the cell temperature notifying signals that are output from the temperature controller 2. This process is conducted until the temperatures of the respective reaction cells 24 reach the reference temperature. It should be noted that the reference temperature is set appropriately according to a kind of the sample and a kind of the measurement item.

Next, when the temperatures of the respective cells 24 reach the reference temperature, the measurement apparatus 12 allows the laser driving part 19 to drive the laser 62 so as to irradiate the seal 36a with its laser beam. When the seal 36b is broken, the sample flows into the reaction cell 24 via the flow path 23, and reacts with the reagent 25. Thereafter, the measurement apparatus 12 measures the absorbance and calculates the density of the component.

As described above, according to the analyzer of Embodiment 1, the sample and the reagent 25 can react with each other after the temperatures of the reaction cells 24 reach the reference temperature. In particular, in the case where reagent 15 is disposed in a state of being solidified in the reaction cell 24, since a speed of dissolving or dispersing the reagent into the sample can be maintained to be constant, the reaction with excellent reproducibility can be achieved. Further, in the case of specifying the density of the object material by the measurement of a reaction speed, like the measurement of some enzyme activities, since the temperatures of the reaction cells 24 can be maintained to be constant from the time when starting the measurement to the time when terminating the measurement, the reaction speed can be measured precisely.

In Embodiment 1, the infrared sensor 1 is not limited to the thermopile-type infrared sensor. As the infrared sensor 1, heat-type infrared sensors other than the thermopile-type infrared sensor, and quantum-type infrared sensors also can be used. Specifically, as the heat-type infrared sensors other than the thermopile-type infrared sensor, pyroelectric infrared sensors and bolometer-type infrared sensors are exemplified. Moreover, as the quantum-type infrared sensors, for example, photoelectromotive force-type infrared sensors using InAs or InSb as a material, photoconductive infrared sensors and the like are exemplified.

Moreover, the infrared sensor 1 may be disposed at a position where the infrared ray 9 that is emitted from the reaction cell 24 can be photoreceived, and the position of the of the infrared sensor 1 is not limited particularly. However, in the light of the improvement of the precision of the measurement temperature, it is preferable to dispose the infrared sensor 1 at a position facing the reaction cell 24 in a thickness direction of the analyzing tool 10, in a state where a photoreceptive surface of the infrared sensor 1 faces the reaction cell 24. In addition, in order to avoid an effect of the heat charged from the heating element 33, it is particularly preferable to dispose the infrared sensor 1 directly underneath the reaction cell 24 on a side where the heating element 33 is not provided (that is, the substrate 21 side), as shown in FIG. 5, Further, it is preferable to dispose the photoreceptive surface of the infrared sensor 1 as near as possible to the analyzing tool 10, as long as it does not contact with the analyzing tool 10. Specifically, a distance between the photoreceptive surface of the infrared sensor 1 and the analyzing tool 10 (a distance between the photoreceptive surface of the infrared sensor 1 and the bottom surface of the concave part 27 in the example of FIG. 5) L preferably is set within a range from 0.1 mm to 30 mm, and particularly preferably is set within a range from 0.5 mm to 5 mm.

Moreover, if a lens system for condensing the infrared rays is disposed between the infrared sensor 1 and the analyzing tool 10, the distance L can be set according to the lens system.

Moreover, in order to enhance the precision of the temperature to be measured, it is preferable that a thickness t of the analyzing tool 10 in a part where the reaction cell 24 is provided on the infrared sensor 1 side is thinnest possible as long as a strength of the analyzing tool 10 can be secured. For example, if the analyzing tool 10 is formed of an optically transparent resin material, the thickness t preferably is set within a range from 0.01 mm to 5 mm, and particularly preferably is set within a range from 0.5 mm to 1 mm. Moreover, the substrate 21 also can be formed by providing projections and depressions on a transparent resin sheet, and in this case, the thickness t can be 0.1 mm or less easily.

Further, in Embodiment 1, the infrared sensor 1 is supported by a supporting member, which is not illustrated in FIG. 5. In order to suppress unnecessary radiant heat from being incident into the infrared sensor 1 and an increase of a temperature of the infrared sensor 1 itself caused thereby, it is preferable that the supporting member can reflect such radiant heat. Specifically, it is preferable that a surface of the supporting member is coated with gold, aluminum or the like. Moreover, in order to protect the infrared sensor 1 from a temperature change around it, the supporting member preferably is formed of a material having excellent heat insulation, for example, a resin material and a rubber material.

Moreover, the one infrared sensor 1 is provided in the example shown in FIG. 5, but a plurality of the infrared sensors 1 also can be used in Embodiment 1. Also, the reaction cell 24 whose temperature is measured can be switched by rotating the analyzing toll 10 with the above-described rotation mechanism.

Moreover, there is a case where a disturbance infrared ray 11 is present, as shown in FIG. 5. In such a case, when the infrared sensor 1 photoreceives the disturbance infrared ray 11, the precision of the measured temperature may be lessen. Thus, the substrate 21 and the cover 31 preferably are formed of a material that is not transparent with respect to the disturbance infrared ray 11, for example, a resin material such as a polystyrene (PS) resin, a polymethyl methacrylate (PMMA) resin, a polyethylene resin and a polypropylene resin.

Moreover, in the example of FIG. 5, the measurement apparatus 12 is provided with only one each (one pair) of the light emitting device 7 and the photoreceptive device 8, but Embodiment 1 is not limited to this example. In Embodiment 1, the measurement apparatus 12 may be provided with plural sets of the light emitting devices 7 and the photoreceptive devices 8. In this case, in order to enable the measurements on a plurality of the measurement items at once, it is preferable that the irradiation and the photoreception of light with different wavelengths can be achieved by each group.

Embodiment 2

Figure 6:
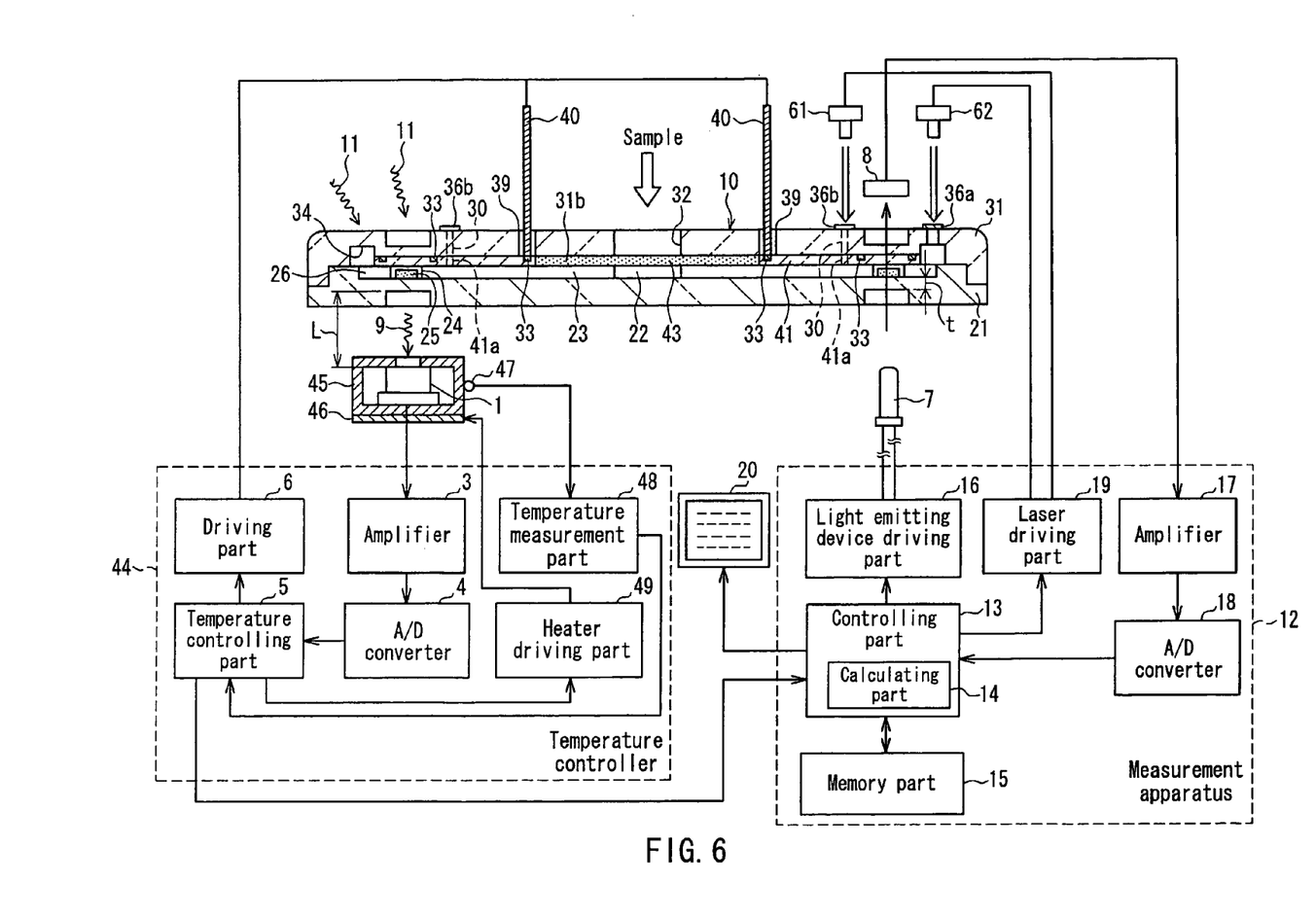
FIG. 6 is a diagram schematically showing a structure of an analyzer of Embodiment 2 of the present invention.

Next, an analyzer of Embodiment 2 of the present invention will be described below with reference to FIG. 6. FIG. 6 is a diagram schematically showing a structure of the analyzer of Embodiment 2 of the present invention. In FIG. 6, the same components as those described with reference to FIGS. 1 to 5 are denoted with the same reference numerals as those therein.

As shown in FIG. 6, the analyzer of Embodiment 2 also is provided with the analyzing tool 10 shown in FIGS. 1 to 4 and the measurement apparatus 12 shown in FIG. 5, similarly to the analyzer of Embodiment 1. Moreover, a temperature controller 44 that is provided in the analyzer of Embodiment 2 also controls the temperature of the reaction cell 24 by using the infrared sensor 1.

However, in Embodiment 2, the temperature controller 44 also can control the temperature of the infrared sensor 1 unlike Embodiment 1. Except for this point, the analyzer of Embodiment 2 is structured similarly to the analyzer of Embodiment 1. Distinctive points from Embodiment 1 will be described below specifically.

As shown in FIG. 6, the infrared sensor 1 is stored inside a case 45 unlike Embodiment 1. In the case 45 for storing the infrared sensor 1, a heater 46 for heating the case 45 and a temperature sensor 47 for measuring a temperature of the case 45 are attached. Moreover, the case 45 is formed of a metal or a resin such that a heat capacity thereof is larger than that of the infrared sensor 1.

Moreover, the temperature controller 44 further is provided with a heater driving part 49 and a temperature measurement part 48 unlike that of Embodiment 1. The heater driving part 49 applies a voltage to the heater 46 according to the instruction from the temperature controlling part 5. Moreover, the temperature sensor 47 outputs an analog signal (a case temperature notifying signal) according to the temperature of the case 45 to the temperature measurement part 48. The temperature measurement part 48 performs A/D conversion with respect to the case temperature notifying signal from the temperature sensor 46, and outputs the case temperature notifying signal that is converted into a digital signal to the temperature controlling part 5. The temperature controlling part 5 drives the heater driving part 49 based on the case temperature notifying signal from the temperature measurement part 48 such that the temperature of the case 45 is maintained at a set temperature.

As described above, in Embodiment 2, the temperature controlling part 5 performs feed-back control such that the temperature of the case 45 for storing the infrared sensor 1 is adjusted to be constant. As a result, temperatures of the infrared sensor 1 and a thermistor (not illustrated) that is provided therein are maintained to be constant. Thus, according to Embodiment 2, the temperature of the reaction cell 24 can be measured more precisely, compared with Embodiment 1. Also, the analyzer of Embodiment 2 can obtain effects that can be obtained by the analyzer of Embodiment 1.

In Embodiments 1 and 2 described above, the analyzer is provided with the two apparatuses, which are the temperature controller and the measurement apparatus, but these two apparatuses also can be replaced with an apparatus that is provided with one CPU. In this case, the one CPU functions as the temperature controlling part of the temperature controller and the controlling part of the measurement apparatus.

Moreover, in the present invention, the analyzer is not limited to the apparatus for analyzing a component by measuring absorption. Besides this, the analyzer of the present invention also may be a fluorometer that requires precise temperature control on a device, an electrolyte meter, a liquid chromatography meter or the like. Further, the analyzer of the present invention also can be applied to an apparatus for achieving a method that requires dynamic temperature control, such as a gene amplification method.

Industrial Applicability

As described above, since the temperature of the reaction cell can be controlled more strictly by using the analyzer of the present invention, compared with a conventional one, the precision of the analysis of the analyzer can be improved. The analyzer of the present invention has industrial applicability.

The invention claimed is:
1. An analyzer for analyzing a sample that reacts with a reagent, the analyzer comprising:
an analyzing tool;
an infrared sensor;
a temperature controlling part; and
a measurement apparatus for analyzing a density of a certain component in the sample that reacts with the reagent in the reaction cell,
wherein
the analyzing tool comprises: a plurality of the reaction cells in which the sample and the reagent react with each other; and a heating element that is heated by electrification, inside the analyzing tool,
the infrared sensor is disposed outside the analyzing tool so as to photoreceive an infrared ray that is emitted from the reaction cell, and outputs a signal that is in accordance with an amount of the photoreceived infrared ray to the temperature controlling part, the temperature controlling part adjusts a heat value of the heating element based on the signal from the infrared sensor, the temperature controlling part specifies a temperature of the reaction cell based on the signal that is output from the infrared sensor to the temperature controlling part, and notifies the specified temperature and information for specifying the reaction cell whose temperature is measured to the measurement apparatus, and the measurement apparatus comprising a memory part and a calculating part that are configured to correct a calculated value for the density of a certain component in the sample per each reaction cell based on the temperature and the information that is notified by the temperature controlling part.

2. The analyzer according to claim 1, wherein the analyzing tool is formed of an optically transparent material, and further comprises:

an inlet for introducing the sample into an inside of the analyzing tool;

a storage part for storing the introduced sample temporarily; and a flow path for transferring the stored sample into the reaction cell.

3. The analyzer according to claim 2, wherein the analyzing tool is formed to have a disk shape, the inlet and the storage part are disposed so as to be positioned at a center of the disk, a plurality of the reaction cells are provided, each of the reaction cells is disposed on a periphery of the storage part along a circumferential direction of the disk, and a plurality of the flow paths are provided in a radial manner.

4. The analyzer according to claim 2, wherein the infrared sensor is disposed at a position that faces the reaction cell in a thickness direction of the analyzing tool in a state where a photoreceptive surface of the infrared sensor faces the reaction cell, a thickness of the analyzing tool in a part where the reaction cell is provided on the infrared sensor side is set within a range from 0.01 mm to 5 mm.

5. The analyzer according to claim 4, wherein a distance between the photoreceptive surface of the infrared sensor and the analyzing tool is set within a range from 0.1 mm to 30 mm.

6. The analyzer according to claim 1, wherein the infrared sensor is a thermopile-type infrared sensor.

7. The analyzer according to claim 1, wherein the measurement apparatus comprises a memory part for storing a correction factor group that is set for each temperature, specifies a corresponding correction factor among the stored correction factor group based on the temperature that is notified by the temperature controlling part, and multiplies the specified correction factor by the measured reactivity so as to correct the measured reactivity.

8. The analyzer according to claim 2, further comprising a measurement apparatus for measuring reactivity of the sample that reacts with the reagent in the reaction cell, wherein the analyzing tool comprises a blocking part for blocking an inflow of the sample into the reaction cell, the temperature controlling part specifies a temperature of the reaction cell based on a signal that is output from the infrared sensor to the temperature controlling part, and notifies the specified temperature to the measurement apparatus, and the measurement apparatus cancels the blocking by the blocking part when the temperature that is notified by the temperature controlling part reaches a reference temperature.

9. The analyzer according to claim 1, further comprising: a case for storing the infrared sensor; a heater for heating the case; and a temperature sensor for outputting a case temperature notifying signal that depends on a temperature of the case to the temperature controlling part, wherein the temperature controlling part drives the heater based on the signal from the temperature sensor, and adjusts a temperature of the infrared sensor.

* * * * *